(12) United States Patent
Ranchal et al.

(10) Patent No.: US 11,250,939 B2
(45) Date of Patent: Feb. 15, 2022

(54) MANAGING PERSONALIZED SUBSTANCE ADMINISTRATION

(71) Applicant: International Business Machines Corporation, Armonk, NY (US)

(72) Inventors: Rohit Ranchal, Cambridge, MA (US); Fang Lu, Billerica, MA (US); Paul R. Bastide, Ashland, MA (US); Grant Covell, Belmont, MA (US)

(73) Assignee: International Business Machines Corporation, Armonk, NY (US)

( * ) Notice: Subject to any disclaimer, the term of this patent is extended or adjusted under 35 U.S.C. 154(b) by 96 days.

(21) Appl. No.: 16/248,218

(22) Filed: Jan. 15, 2019

(65) Prior Publication Data
US 2020/0227154 A1    Jul. 16, 2020

(51) Int. Cl.
*G16H 20/13*    (2018.01)
*G06Q 10/10*    (2012.01)
*G16H 10/60*    (2018.01)
*G06N 20/00*    (2019.01)
*G06N 3/08*    (2006.01)

(52) U.S. Cl.
CPC ............. *G16H 20/13* (2018.01); *G06N 3/086* (2013.01); *G06N 20/00* (2019.01); *G06Q 10/109* (2013.01); *G16H 10/60* (2018.01)

(58) Field of Classification Search
None
See application file for complete search history.

(56) References Cited

U.S. PATENT DOCUMENTS

| | | | |
|---|---|---|---|
| 5,950,630 A | 9/1999 | Portwood et al. | |
| 7,809,585 B1 | 10/2010 | Ghouri | |
| 9,256,910 B2 | 2/2016 | Goldberg | |
| 9,679,113 B2 | 6/2017 | Hanina et al. | |
| 9,865,176 B2 | 1/2018 | Tran | |

(Continued)

FOREIGN PATENT DOCUMENTS

| | | | | |
|---|---|---|---|---|
| CA | 2609434 A1 | * | 12/2006 | ............. G16H 50/50 |
| WO | 2014165206 A1 | | 10/2014 | |
| WO | 2017211581 A1 | | 12/2017 | |

OTHER PUBLICATIONS

"VA/DoD Clinical Practice Guideline for the Management of Substance User Disorders", Dept of Veteran Affairs, Department of Defense, Version 3.0, Dec. 2015, 169 pages.

(Continued)

*Primary Examiner* — Lena Najarian
(74) *Attorney, Agent, or Firm* — Aaron Pontikos; Edell, Shapiro & Finnan, LLC

(57) ABSTRACT

A computer system manages administration of substances. Information is received including administration of one or more substances and user preferences for the administration. Features of the received information are extracted, and interactions between the one or more substances and a new substance for administration are identified based on the extracted features. A schedule is generated for administration of the one or more substances and the new substance based on the interactions. Embodiments of the present invention further include a method and program product for managing administration of substances in substantially the same manner described above.

20 Claims, 5 Drawing Sheets

(56) References Cited

U.S. PATENT DOCUMENTS

| | | | |
|---|---|---|---|
| 9,977,870 B2 | 5/2018 | Hanina et al. | |
| 2003/0163353 A1* | 8/2003 | Luce | G16H 20/10 |
| | | | 705/2 |
| 2004/0049407 A1* | 3/2004 | Rosenberg | G06Q 10/10 |
| | | | 705/2 |
| 2008/0172253 A1* | 7/2008 | Chung | G06Q 10/0875 |
| | | | 705/3 |
| 2009/0055221 A1* | 2/2009 | Loftus | G16H 15/00 |
| | | | 705/3 |
| 2012/0115914 A1* | 5/2012 | Nelson | A61P 25/00 |
| | | | 514/357 |
| 2017/0351842 A1* | 12/2017 | Booth | G16H 40/63 |
| 2018/0060517 A1* | 3/2018 | Bagwell | G16H 70/40 |
| 2018/0214048 A1 | 8/2018 | Zdeblick et al. | |

OTHER PUBLICATIONS

Kleber et al., "Practice Guideline for the Treatment of Patients with Substance Use Disorders", Second Edition, American Psychiatric Association, 2010, 276 pages.

Anonymously, "System and Method for Patients to Self-Adjust Treatments", IP.com Prior Art Database Technical Disclosure, IPCOM000247999D, Oct. 14, 2016, 13 pages.

Anonymously, "Method and System for Optimizing Organizational Interaction and Providing Proactive Recommendations", IP.com Prior Art Database Technical Disclosure, IPCOM000229323D, Jul. 22, 2013, 4 pages.

Siemens et al., "Patient Process Module in Clinical Workflow Simulation Tool for Healthcare Institutions", IP.com Prior Art Database Technical Disclosure, IPCOM000146857D, Mar. 25, 2007, 4 pages.

"Grapefruit Juice and Some Drugs Don't Mix", FDA Consumer Update, U.S. Food & Drug Administration, https://www.fda.gov/ForConsumers/ConsumerUpdates/ucm292276.htm, Jul. 18, 2017, 2 pages.

Jara et al., "Drug identification and interaction checker based on IoT to minimize adverse drug reactions and improve drug compliance", http://people.cs.pitt.edu/~chang/231/y14/internetThings.pdf, Personal and Ubiquitous Computing 18.1 (2014): 5-17.

Drug Interactions, Drugs.com, https://www.drugs.com/drug_interactions.php, retrieved from internet Jan. 2019, 3 pages.

Drug Interaction Checker, WebMD LLC, http://www.webmd.com/interaction-checker/, retrieved from internet Jan. 2019, 6 pages.

Drug Interactions Checker, Drugs.com, https://www.drugs.com/drug_interactions.html, retrieved from internet Jan. 2019, 4 pages.

* cited by examiner

MANAGING PERSONALIZED SUBSTANCE ADMINISTRATION

BACKGROUND

1. Technical Field

Present invention embodiments relate to administration of substances, and more specifically, to processing information to manage personalized administration of substances.

2. Discussion of the Related Art

A drug interaction is a situation in which a substance affects the activity of another substance when both are administered together. This action can be synergistic (when a substance's effect is increased) or antagonistic (when a substance's effect is decreased), or a new effect can be produced that neither substance produces on its own. Interactions may occur between one medication and another, between medications and foods, or between medications and medicinal plants, such as herbs. An individual may typically administer substances on a predetermined schedule throughout the day. However, it is difficult for an individual to adhere to a proper schedule when the individual consumes other substances that can affect their administration schedule.

SUMMARY

According to one embodiment of the present invention, a computer system manages administration of substances. Information is received including administration of one or more substances and user preferences for the administration. Features of the received information are extracted, and interactions between the one or more substances and a new substance for administration are identified based on the extracted features. A schedule is generated for administration of the one or more substances and the new substance based on the interactions. Embodiments of the present invention further include a method and program product for managing substance administration in substantially the same manner described above.

BRIEF DESCRIPTION OF THE DRAWINGS

Generally, like reference numerals in the various figures are utilized to designate like components.

DETAILED DESCRIPTION

Present invention embodiments relate to managing administration of substances, and more specifically, to processing information to manage personalized administration of substances. A substance, as used herein, may refer to any item, such as a medication, food, herbal remedy, and the like, that can produce a drug interaction when administered with another substance. For example, if a patient consumes *ginseng* while using warfarin, then the patient may experience an elevated risk of bleeding. Additionally, the time at which a substance is administered may be important, even in the absence of concerns about interactions. For example, administering doxycycline to a patient prior to the patient's bedtime may result in esophagitis.

Present invention embodiments process information relating to the administration of various substances to a user in order to generate a personalized administration schedule for the user. The user's daily prescribed substances, daily routine, and preferences are considered, and new substances are evaluated against substances that have already been administered to the user in order to provide a schedule that identifies optimal times and dosages for both the new and existing substances.

It should be noted that references throughout this specification to features, advantages, or similar language herein do not imply that all of the features and advantages that may be realized with the embodiments disclosed herein should be, or are in, any single embodiment of the invention. Rather, language referring to the features and advantages is understood to mean that a specific feature, advantage, or characteristic described in connection with an embodiment is included in at least one embodiment of the present invention. Thus, discussion of the features, advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages will become more fully apparent from the following drawings, description and appended claims, or may be learned by the practice of embodiments of the invention as set forth hereinafter.

Figure 1:
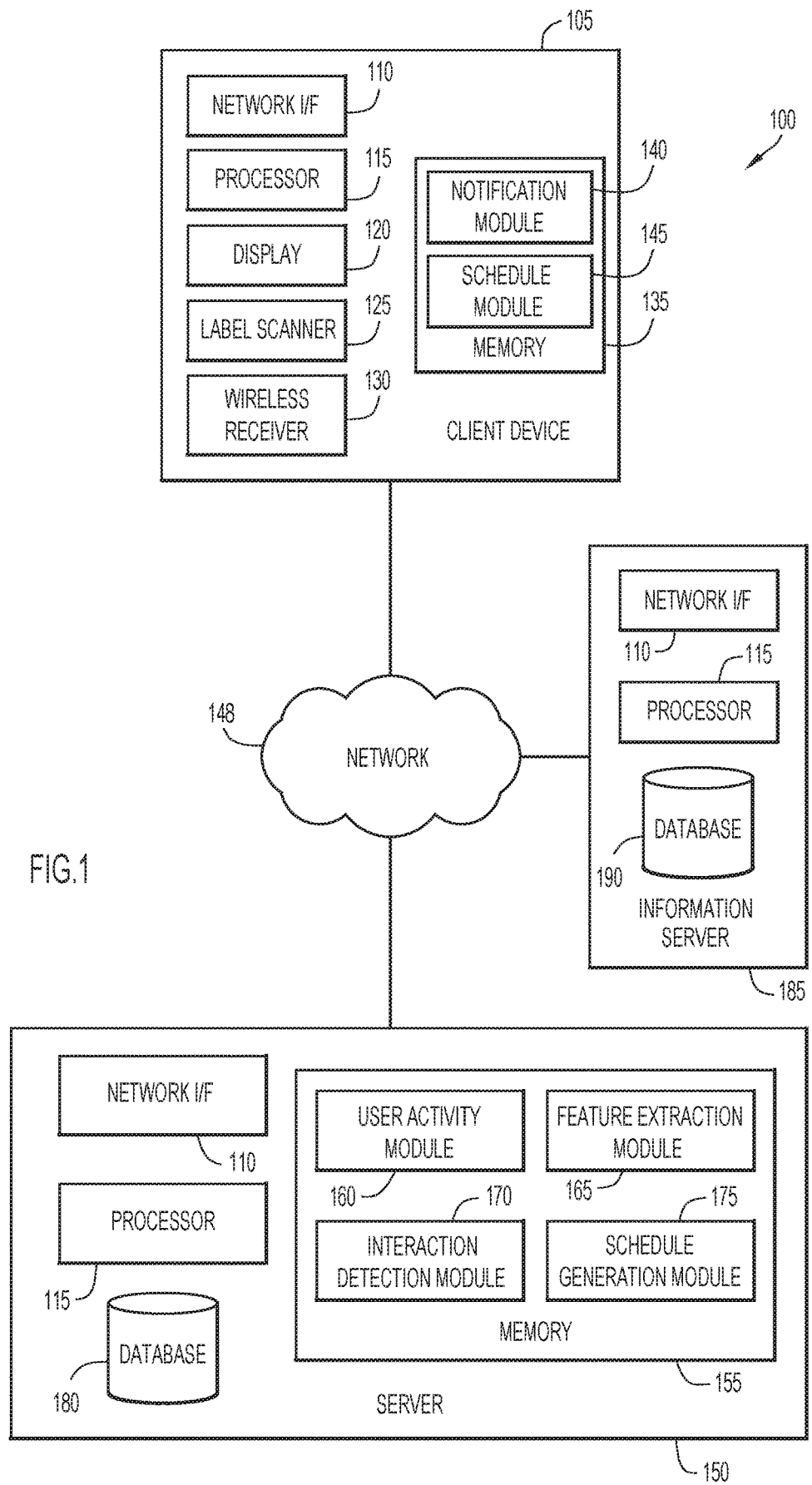
FIG. 1 is a block diagram depicting a computing environment for processing substance administration information in accordance with an embodiment of the present invention.

Present invention embodiments will now be described in detail with reference to the Figures. FIG. 1 is a block diagram depicting a computing environment 100 for processing substance administration information in accordance with an embodiment of the present invention. As depicted, computing environment 100 includes a user device 105, a server 150, and at least one information server 185. It is to be understood that the functional division among components of computing environment 100 have been chosen for purposes of explaining present invention embodiments and is not to be construed as a limiting example.

User device 105 includes a network interface 110, at least one processor 115, a display 120, a label scanner 125, a wireless receiver 130, and memory 135. Memory 135 may include notification module 140 and schedule module 145. User device 105 may include a laptop computer, a tablet computer, a netbook computer, a personal computer (PC), a desktop computer, a personal digital assistant (PDA), a smart phone, or any programmable electronic device capable of executing computer readable program instructions. Network interface 110 enables components of user device 105 to send and receive data over a network, such as network 148. User device 105 may include internal and external hardware components, as depicted and described in further detail with respect to FIG. 5.

Display 120 may include any electronic device capable of presenting information in a visual form. For example, display 120 may be a liquid crystal display (LCD), a cathode ray tube (CRT) display, a light-emitting diode (LED) display, an electronic ink display, and the like. Information relating to a user's substance administration schedule may be presented to a user of user device 105 via display 120.

Label scanner 125 may include any optical device for scanning labels to obtain information. Label scanner 125 may include a camera-based reader, a laser scanner, and the like. Label scanner 125 may scan any label affixed or otherwise associated with a substance, such as a one dimensional barcode, two dimensional barcode (e.g., data matrix barcode), or any other label in which information may be visually encoded. For example, label scanner 125 may scan a label printed on the packaging of a particular multivitamin, enabling user device 105 to identify the multivitamin as a substance that a user may consume.

User device 105 may wirelessly receive data via wireless receiver 130. Wireless receiver 130 may include any radio-frequency or other receiver. In some embodiments, wireless receiver 130 is a radio frequency identification (RFID) reader used to read passive or active RFID tags. User device 105 may receive information corresponding to a substance via wireless receiver 130. For example, wireless receiver 130 may scan an RFID tag associated with the packaging of a particular over-the-counter medication, enabling user device 105 to identify the over-the-counter medication as a substance that a user may consume.

Notification module 140 and schedule module 145 may include one or more modules or units to perform various functions of present invention embodiments described below. Notification module 140 and schedule module 145 may be implemented by any combination of any quantity of software and/or hardware modules or units, and may reside within memory 135 of user device 105 for execution by a processor, such as processor 115.

Notification module 140 may send notifications to a user of user device 105 relating to the user's substance administration schedule. Notification module 140 may provide a visual notification that is presented on display 120 when a user is scheduled to administer a substance. For example, notification module 140 may present text on display 120 to inform a user to administer a particular substance, such as "it is time to drink a glass of water," "take a multi-vitamin this morning," and the like. In some embodiments, user device 105 may play a particular sound, may vibrate, and/or may activate a light to notify a user.

Schedule module 145 may enable a user of user device 105 to access and modify a substance administration schedule. Schedule module 145 may present a substance administration schedule that includes one or more administration events over a selected period of time. The substance may include a food, drink, or a composite of multiple individual substances, which are mapped to known ingredients. In some embodiments, schedule module 145 presents a user's substance administration schedule in the form of a calendar or daily planner. A user may input the names of any substances that the user has administered using schedule module 145, as well as any substances that the user plans on administering. When a user inputs an administered substance, the user may input a time of administration, an amount of administration, and the name of the substance administered, including the chemical name (e.g., International Union of Pure and Applied Chemistry (IUPAC) name) of a substance, the generic name of a substance, and/or the trade name of a substance. In some embodiments, schedule module 145 may present a schedule to a user as a graphical timeline of events, with each event corresponding to the administration of one or more substances. Schedule module 145 may depict a graphical timeline that includes ranges of times in which substances may be administered.

Network 148 may include a local area network (LAN), a wide area network (WAN) such as the Internet, or a combination of the two, and includes wired, wireless, or fiber optic connections. In general, network 148 can be any combination of connections and protocols known in the art that will support communications between user device 105, server 150, and/or information server 185 via their respective network interfaces 110 in accordance with embodiments of the present invention.

Server 150 includes a network interface 110, at least one processor 115, memory 155, and a database 180. Memory 155 includes a user activity module 160, a feature extraction module 165, an interaction detection module 170, and a schedule generation module 175. In various embodiments of the present invention, server 150 may include a laptop computer, a tablet computer, a netbook computer, a personal computer (PC), a desktop computer, a personal digital assistant (PDA), a smart phone, a thin client, or any programmable electronic device capable of executing computer readable program instructions. Network interface 110 enables components of server 150 to send and receive data over a network, such as network 148. Server 150 may include internal and external hardware components, as depicted and described in further detail with respect to FIG. 5.

User activity module 160, feature extraction module 165, interaction detection module 170, and schedule generation module 175 may include one or more modules or units to perform various functions of present invention embodiments described below. User activity module 160, feature extraction module 165, interaction detection module 170, and schedule generation module 175 may be implemented by any combination of any quantity of software and/or hardware modules or units, and may reside within memory 155 of server 150 for execution by a processor, such as processor 115.

User activity module 160 may obtain and manage information relating to any substances that are administered to a user. The information may include the name of the substance, the amount of the substance that was administered, and/or the time of administration. User activity module 160 may obtain information from user device 105 when a user logs a substance that the user has administered. A user may log a substance by manually inputting the name of the substance to user device 105, by scanning a label associated with a substance using label scanner 125, and/or by scanning an RFID tag associated with a substance using wireless receiver 130. For example, a user who is diabetic may log an amount (e.g., a dosage) of insulin that the user has administered and a time of administration.

In some embodiments, user activity module 160 accesses one or more other servers to receive information relating to a user's substance administration. For example, user activity module 160 may access a server, such as information server 185, to receive substance administration information pertaining to a user. The accessed server may include any server with which a user shares health information. For example, when a user logs dietary information into a fitness tracking application that stores a user's information on a server, user activity module 160 may access the fitness tracking application's server.

Feature extraction module 165 may extract features of administered substances that may be relevant to the identification of interactions between substances. Extracted features may include any aspects of a substance that are known to potentially lead to interactions, including any active and inactive ingredients, chemical compounds, elements, and the like. Feature extraction module 165 may consult one or more databases, such as database 180, in order to extract features. For example, when user activity module 160 determines that a user has administered a particular nonsteroidal anti-inflammatory drug (NSAID), user activity module 160 may query a database using the name of the drug to identify features of the drug, which may include acetylsalicylic acid and caffeine as active ingredients, and dextrose, cellulose, and indigo carmine as inactive ingredients.

Interaction detection module 170 may analyze the extracted features of administered substances to identify interactions. Interaction detection module 170 may consult a database, such as database 180, to determine whether there is a potential interaction between two or more substances based on the extracted features. Interaction detection module 170 may also determine a magnitude of an interaction based on the volume of each substance that is administered and the time of administration. For example, interaction detection module 170 may determine that atorvastatin interacts with furanocoumarins, which are a class of organic compounds that feature extraction module 165 may have extracted as a feature of grapefruit juice.

Schedule generation module 175 may generate a personalized substance administration schedule for a user, as well as modify a user's schedule in response to the administration of substances. Schedule generation module 175 may generate a schedule based on a user's preferences regarding substance administration and/or based on a user's actual administration schedule. For example, a user may indicate (e.g., via schedule module 145 of user device 105) that the user prefers to administer a particular substance, such as a multivitamin, in the mornings, and prefers to administer a prescribed medication, such as an antibiotic, after having lunch. A user may also indicate any other substances, including complementary substances, that the user administers along with a substance. Additionally or alternatively, a user may log one or more substance administration events on an ad hoc basis throughout the user's day, or a user's substance administration timeline may be provided by an information server. In some embodiments, schedule generation module 175 may add substances to a user's schedule. Schedule generation module 175 may indicate complementary substances to be administered along with a substance. For example, if a particular medication is more effective when a user is hydrated, schedule generation module 175 may add an event in the user's schedule recommending that the user drink a glass of water.

Schedule generation module 175 may process any available substance administration information for a user to generate a personalized substance administration schedule for the user. When generating a substance administration schedule, schedule generation module 175 processes the amount of a substance that is administered and the time of administration, while accounting for a user's metabolism of the substances, to generate a schedule. For example, if a user administers two substances each day, and the two substances pose the risk of a harmful interaction when administered together, schedule generation module 175 may generate a schedule in which the second substance is scheduled to be administered only after the first substance is metabolized by the user. Likewise, if two substances would have a beneficial effect when administered together, schedule generation module 175 may schedule the substances to be administered closely together, or even simultaneously. In order to account for a user's rate of metabolizing substances, schedule generation module 175 may receive and process information relating to a user's height, weight, typical enzyme levels, and any other information relating to a user's ability to metabolize administered substances, including the half-lives of substances.

In some embodiments, schedule generation module 175 creates an optimized schedule using known or other machine learning techniques. Schedule generation module 175 may create a schedule using genetic learning by employing a fitness function to alter learned features according to whether each learned feature is a good fit or a poor fit. The fitness function may be assigned to a set of learned categories of combinations of administered substances. Alternatively or additionally, schedule generation module 175 may employ multi-dimensional allocation and optimization to optimize a schedule.

Schedule generation module 175 may modify a user's substance administration schedule in response to the user administering another substance that may interact with a previously-administered substance and/or a substance that is scheduled to be administered. When a new substance is administered to a user, a new schedule may be generated that incorporates the new substance along with the one or more previously-administered substances. For example, if a user ingests a substance that has an antagonistic interaction with one of the user's prescribed medications, then schedule generation module 175 may schedule the user to administer more of the prescribed medication later in the day (e.g., after the ingested substance has been metabolized), or may schedule the user to take a greater dosage of the prescribed medication at the next administration. In some embodiments, schedule generation module 175 modifies a user's schedule in response to the user administering a new substance by adding another, complimentary substance to the schedule. For example, if a user administers a substance that has a beneficial, synergistic effect in the presence of magnesium, schedule generation module 175 may add a recommendation to a user's schedule to administer a magnesium supplement or to eat a food that is high in magnesium. In some embodiments, schedule generation module 175 dynamically adjusts a user's schedule based on consumption patterns of substances. For example, if a user is prescribed a medication that is supposed to be administered in the morning, but the user instead tends to administer the substance at night, then schedule generation module 175 may alter the user's schedule accordingly.

Database 180 may include any non-volatile storage media known in the art. For example, database 180 can be implemented with a tape library, optical library, one or more independent hard disk drives, or multiple hard disk drives in a redundant array of independent disks (RAID). Similarly, data on database 180 may conform to any suitable storage architecture known in the art, such as a file, a relational database, an object-oriented database, and/or one or more tables. Database 180 may store data corresponding to substances, including features of substances, and interactions between features of substances. Database 180 may also store substance administration schedules of users, user preferences, and user substance administration histories.

Information server 185 includes a network interface 110, at least one processor 115, and a database 190. In general, information server 185 stores and shares information relating to a user's administration of substances, including times and amounts. Information server 185 may include internal and external hardware components, as depicted and described in further detail with respect to FIG. 5. In some embodiments, information server 185 is an electronic health record server, or a server for a health-tracking application or a fitness application. Server 150 and its modules may access information server 185 using an application program interface (API) to retrieve information corresponding to a user's administered substances.

Database 190 may include any non-volatile storage media known in the art. For example, database 190 can be implemented with a tape library, optical library, one or more independent hard disk drives, or multiple hard disk drives in a redundant array of independent disks (RAID). Similarly, data on database 190 may conform to any suitable storage architecture known in the art, such as a file, a relational database, an object-oriented database, and/or one or more tables. Database 190 may store substance administration schedules of users, substance administration events, user preferences, and user substance administration histories.

Figure 2:
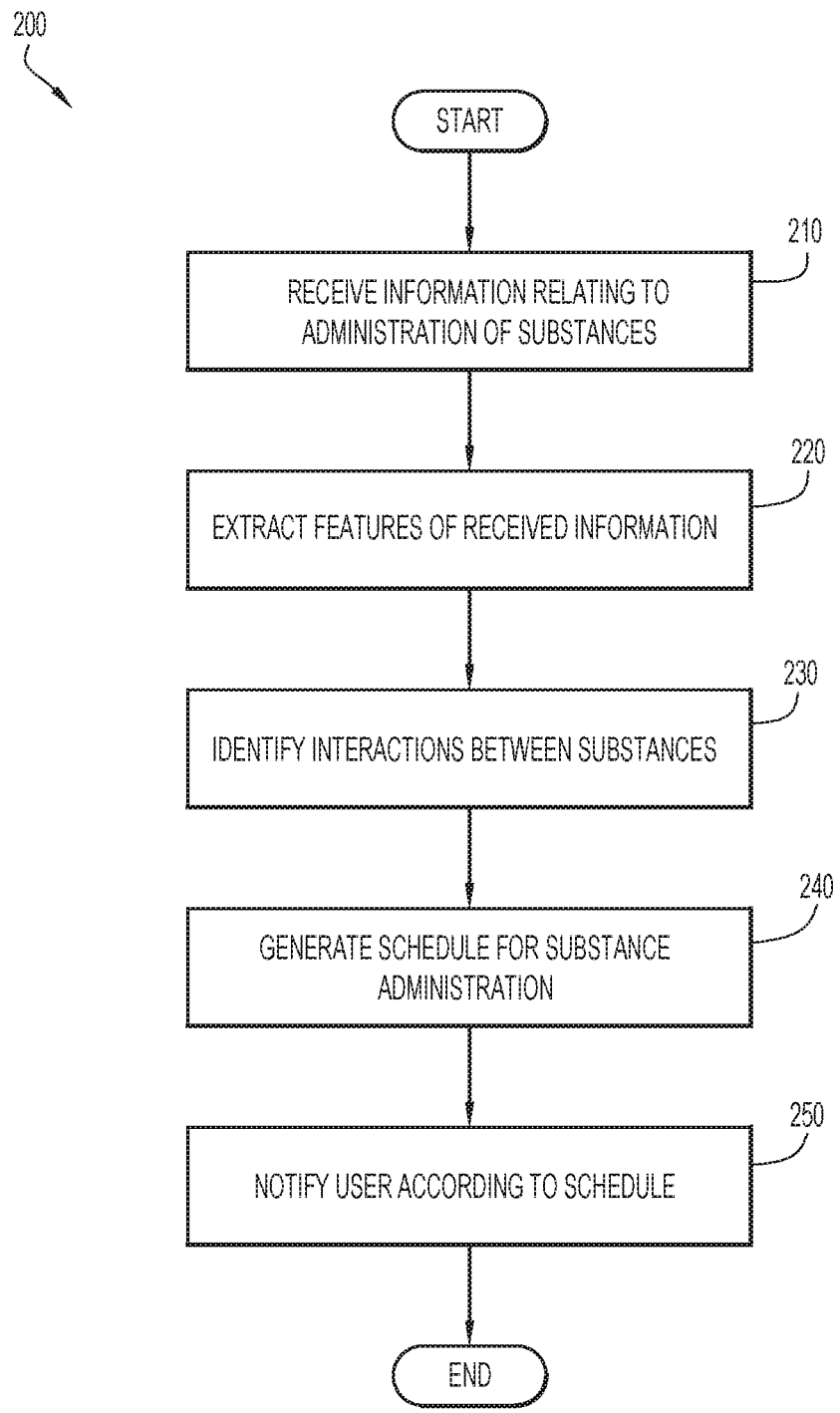
FIG. 2 is a flow chart depicting a method of generating a substance administration schedule in accordance with an embodiment of the present invention.

FIG. 2 is a flow chart depicting a method 200 of generating a substance administration schedule in accordance with an embodiment of the present invention.

Information is received relating to the administration of one or more substances at operation 210. User activity module 160 of server 150 may receive information relating to the administration of substances to a user from user device 105 and/or from information server 185. The information received may include a name of the administered substance, a time of administration, an amount of administration (e.g., dosage), and the like. A substance may include any prescription medication, over-the-counter medication, home remedy, herbal substance, food or beverage, nutraceutical, and the like.

Features of the received information are extracted at operation 220. Feature extraction module 165 may consult a database, such as database 180, to extract features of the information, including any aspects of the substances that are relevant to the identification of interactions. For example, if a user ingests two tablets of a brand name analgesic, extracted features may include the amount of active ingredient(s) in the two tablets (e.g., "200 mg of acetaminophen").

Interactions between substances are identified at operation 230. Interaction detection module 170 may identify interactions between two or more substances by querying database 180 using the extracted features of the substances to determine whether there is a possibility of an interaction. When identifying interactions, interaction detection module 170 may consider any substances that have been administered to the user and that are still being metabolized by a user. By factoring in the user's metabolism and the half-life of an administered substance, interaction detection module 170 can determine whether a substance should be considered. For example, if a user consumed a caffeinated beverage having 100 mg of caffeine, and the half-life of caffeine is five to six hours, then interaction detection module 170 may disregard a user's administration of the caffeinated beverage if the administration occurred twenty-four hours ago, as the user will have metabolized the caffeine.

A personalized substance administration schedule is generated for a user at operation 240. Schedule generation module 175 may generate a schedule listing substances by administration time and by amount. Schedule generation module 175 may generate a schedule that optimizes substance administration by avoiding the administration of substances that have negative interactions. Additionally or alternatively, schedule generation module 175 may generate a schedule that encourages the administration of substances that have positive interactions. Known or other machine learning techniques may be employed to generate a personalized substance administration schedule for a user. The generated schedule may be transmitted to schedule module 145 of user device 105 for viewing by a user The user is notified according to the substance administration schedule at operation 250. Notification module 140 of user device 105 may notify a user when the user is scheduled to administer a substance. In some embodiments, a user may be notified of a particular span of time in which the user should administer a substance. Once a user has administered a substance, the user may provide feedback using user device 105 so that schedule generation module 175 may confirm administration of the substance.

Figure 3:
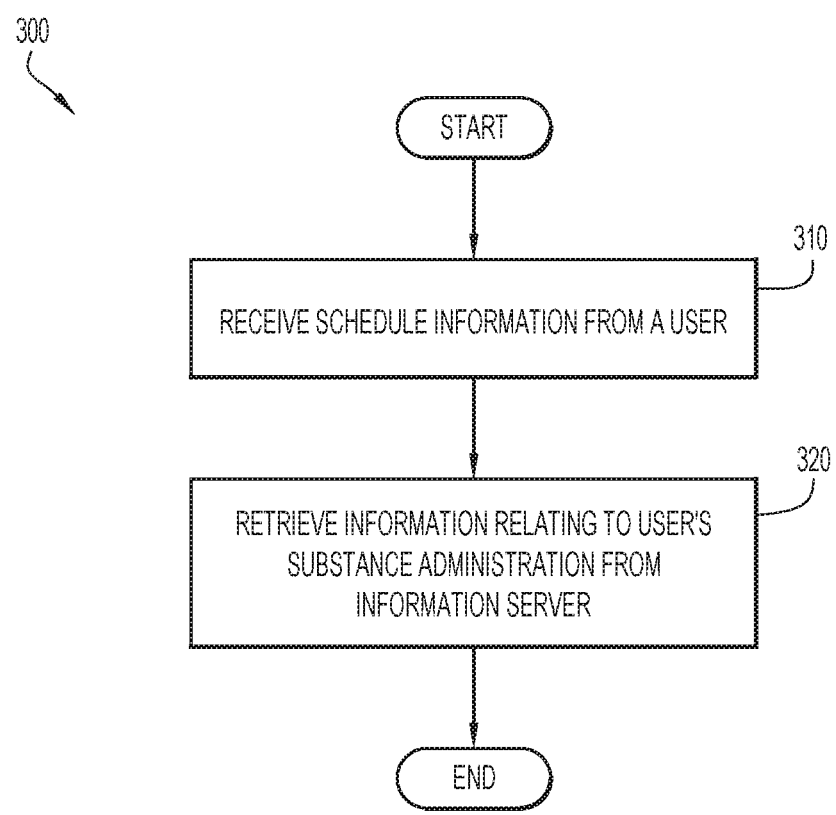
FIG. 3 is a flow chart depicting a method of collecting substance administration information in accordance with an embodiment of the present invention.

FIG. 3 is a flow chart depicting a method 300 of collecting substance administration information in accordance with an embodiment of the present invention.

Schedule information is received from a user at operation 310. Schedule information may include any time preferences for administration of substances, times at which a user is available or unavailable, and dosage frequencies for any medications of the user. A user may provide schedule information via user device 105 that includes the user's daily routine with regard to the administration of substances. For example, a user may indicate that the user takes a particular prescription medication along with multivitamins in the morning, an over-the-counter medication in the afternoon, and drinks an herbal tea in the evening. A user may input information using schedule module 145 of user device 105, which may transmit the information to server 150 for processing.

Information relating to a user's substance administration is retrieved from an information server at operation 320. Information may be stored in a database, such as database 190 of information server 185. The party associated with information server 185 may include a health organization, hospital, health insurance provider, social media website, and the like, and the information may include electronic health records of the user. In some embodiments, the information server may be hosted by a fitness organization with which a user shares substance administration information. For example, a developer of a calorie-counting application may store any information relating to food that a user has consumed and logged using the developer's application. In some embodiments, the information server includes a social media website, and substance administration information is extracted from a user's activity on the website.

Figure 4:
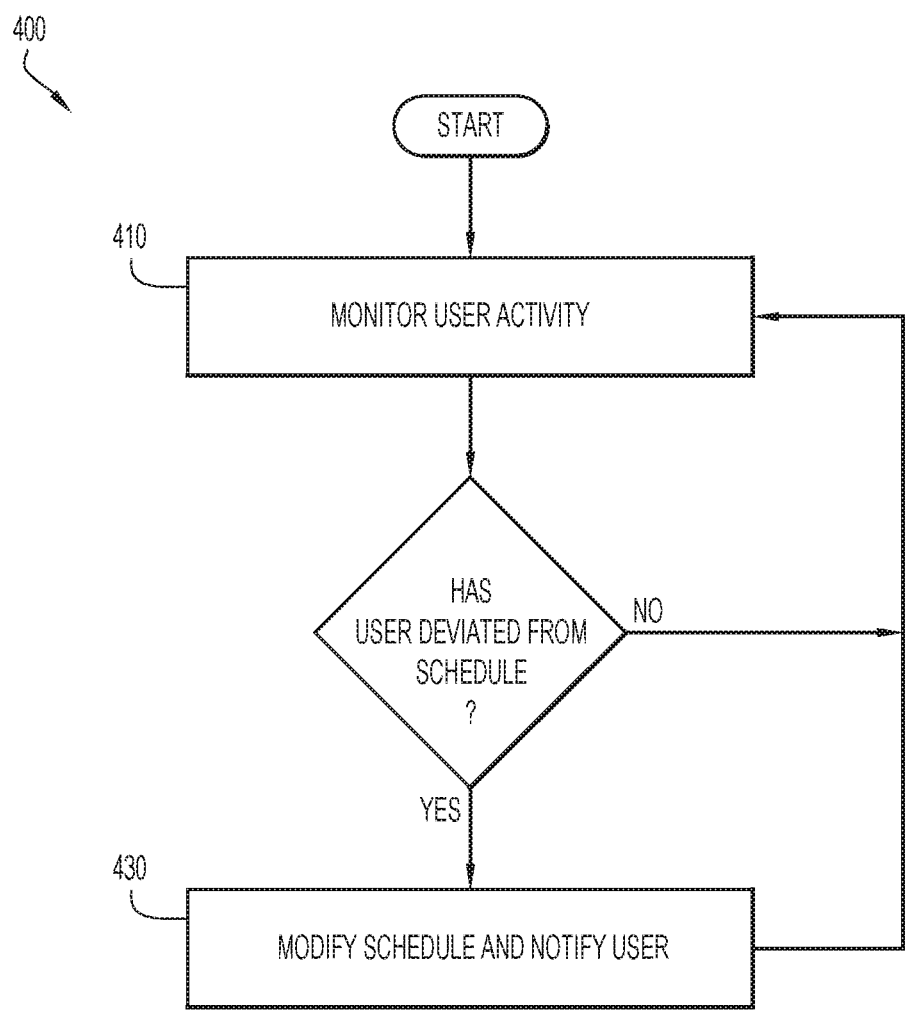
FIG. 4 is a flow chart depicting a method of adjusting a substance administration schedule in accordance with an embodiment of the present invention.

FIG. 4 is a flow chart depicting a method 400 of adjusting a substance administration schedule in accordance with an embodiment of the present invention.

User activity is monitored at operation 410. User activity may be monitored by user activity module 160, which may receive user activity information from user device 105 and/or information server 185. User activity information may include any information relating to the administration of substances to the user, including the name of the administered substance, the time of administration, and the amount of administration.

Operation 420 determines whether the user has deviated from the user's substance administration schedule. If the type of substance administered, time of administration, and/or amount of administration deviate from the user's administration schedule, method 400 proceeds to modify the user's substance administration schedule at operation 430. Deviation from a schedule may include both introducing an unscheduled substance and failing to administer a scheduled substance.

The user's substance administration schedule is modified and the user is notified at operation 430. Interaction detection module 170 may determine whether the deviation from the schedule may result in an interaction. Schedule generation module 175 may then modify the schedule accordingly to generate a new schedule that takes into account previously-administered substances, scheduled substance administrations, and any new substances that have been administered. For example, when a user administers a new substance that was not included in the user's substance administration schedule, schedule generation module 175 may modify the user's substance administration schedule to include the new substance and to account for any interactions the new substance may have with the other administered substances.

Figure 5:
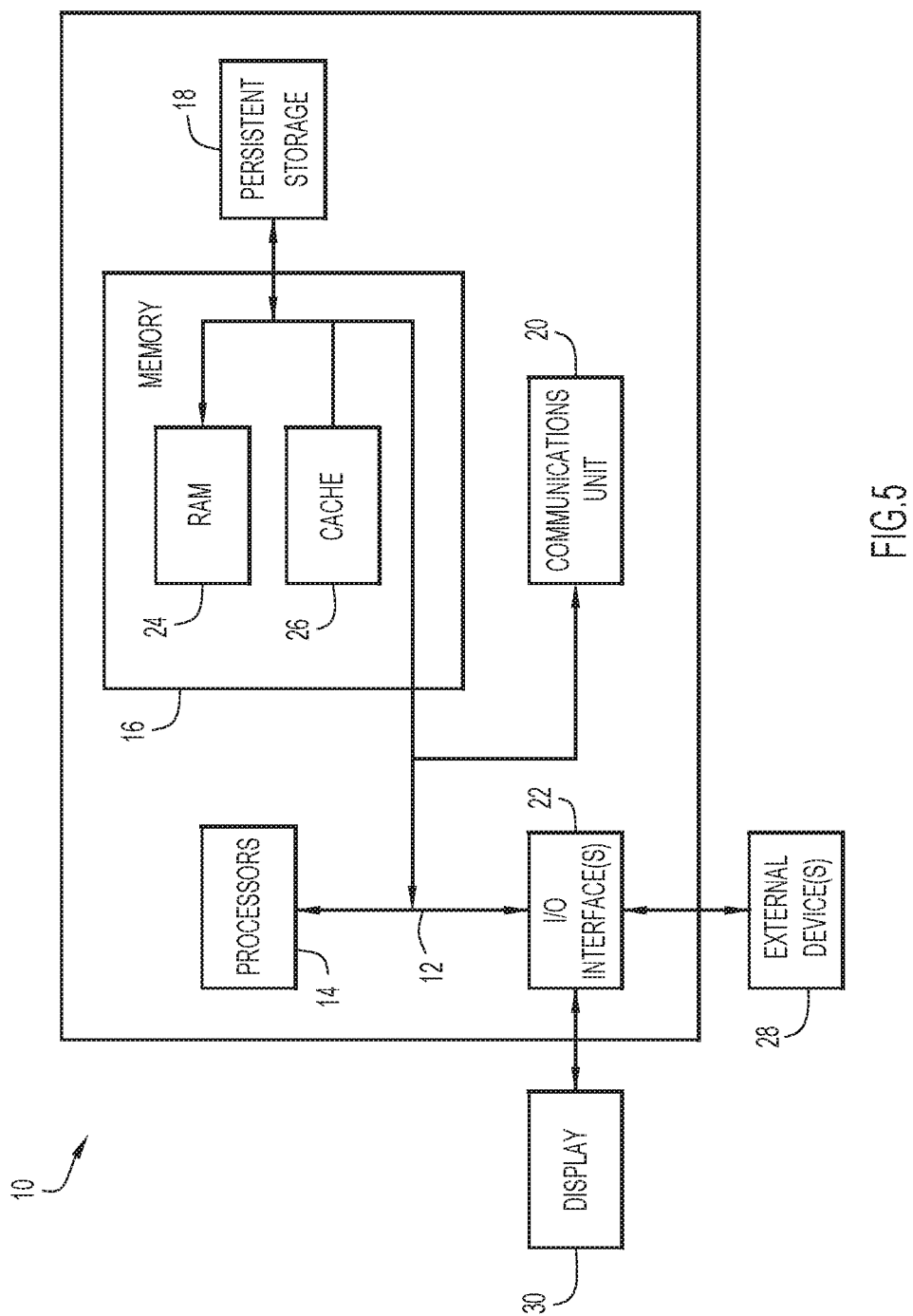
FIG. 5 is a block diagram depicting a computing device in accordance with an embodiment of the present invention.

FIG. 5 is a block diagram depicting components of a computer 10 suitable for executing the methods disclosed herein. Computer 10 may implement user device 105, server 150, and/or information server 185 in accordance with embodiments of the present invention. It should be appreciated that FIG. 5 provides only an illustration of one embodiment and does not imply any limitations with regard to the environments in which different embodiments may be implemented. Many modifications to the depicted environment may be made.

As depicted, the computer 10 includes communications fabric 12, which provides communications between computer processor(s) 14, memory 16, persistent storage 18, communications unit 20, and input/output (I/O) interface(s) 22. Communications fabric 12 can be implemented with any architecture designed for passing data and/or control information between processors (such as microprocessors, communications and network processors, etc.), system memory, peripheral devices, and any other hardware components within a system. For example, communications fabric 12 can be implemented with one or more buses.

Memory 16 and persistent storage 18 are computer readable storage media. In the depicted embodiment, memory 16 includes random access memory (RAM) 24 and cache memory 26. In general, memory 16 can include any suitable volatile or non-volatile computer readable storage media.

One or more programs may be stored in persistent storage 18 for execution by one or more of the respective computer processors 14 via one or more memories of memory 16. The persistent storage 18 may be a magnetic hard disk drive, a solid state hard drive, a semiconductor storage device, read-only memory (ROM), erasable programmable read-only memory (EPROM), flash memory, or any other computer readable storage media that is capable of storing program instructions or digital information.

The media used by persistent storage 18 may also be removable. For example, a removable hard drive may be used for persistent storage 18. Other examples include optical and magnetic disks, thumb drives, and smart cards that are inserted into a drive for transfer onto another computer readable storage medium that is also part of persistent storage 18.

Communications unit 20, in these examples, provides for communications with other data processing systems or devices. In these examples, communications unit 20 includes one or more network interface cards. Communications unit 20 may provide communications through the use of either or both physical and wireless communications links.

I/O interface(s) 22 allows for input and output of data with other devices that may be connected to computer 10. For example, I/O interface 22 may provide a connection to external devices 28 such as a keyboard, keypad, a touch screen, and/or some other suitable input device. External devices 28 can also include portable computer readable storage media such as, for example, thumb drives, portable optical or magnetic disks, and memory cards.

Software and data used to practice embodiments of the present invention can be stored on such portable computer readable storage media and can be loaded onto persistent storage 18 via I/O interface(s) 22. I/O interface(s) 22 may also connect to a display 30. Display 30 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Data relating to substance administration (e.g., substance names, substance administration amounts, substance administration times, user schedule preferences, substance interactions, etc.) may be stored within any conventional or other data structures (e.g., files, arrays, lists, stacks, queues, records, etc.) and may be stored in any desired storage unit (e.g., database, data or other repositories, queue, etc.). The data transmitted between user device 105, server 150, and/or information server 185 may include any desired format and arrangement, and may include any quantity of any types of fields of any size to store the data. The definition and data model for any datasets may indicate the overall structure in any desired fashion (e.g., computer-related languages, graphical representation, listing, etc.).

Data relating to substance administration (e.g., substance names, substance administration amounts, substance administration times, user schedule preferences, substance interactions, etc.) may include any information provided to, or generated by, user device 105, server 150, and/or information server 185. Data relating to substance administration may include any desired format and arrangement, and may include any quantity of any types of fields of any size to store any desired data. The data relating to substance administration may include any data collected about entities by any collection mechanism, any combination of collected information, and any information derived from analyzing collected information.

The present invention embodiments may employ any number of any type of user interface (e.g., Graphical User Interface (GUI), command-line, prompt, etc.) for obtaining or providing information (e.g., data relating to substance administration), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

It will be appreciated that the embodiments described above and illustrated in the drawings represent only a few of the many ways of processing substance administration information to manage personalized administration of substances.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., server software, networking software, notification module 140, schedule module 145, user activity module 160, feature extraction module 165, interaction detection module 170, schedule generation module 175, etc.). These systems may include any types of monitors and input devices (e.g., keyboard, mouse, voice recognition, etc.) to enter and/or view information.

It is to be understood that the software (e.g., server software, networking software, notification module 140, schedule module 145, user activity module 160, feature extraction module 165, interaction detection module 170, schedule generation module 175, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., server software, networking software, notification module 140, schedule module 145, user activity module 160, feature extraction module 165, interaction detection module 170, schedule generation module 175, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., data relating to substance administration). The database system may be implemented by any number of any conventional or other databases, data stores or storage structures (e.g., files, databases, data structures, data or other repositories, etc.) to store information (e.g., data relating to substance administration). The database system may be included within or coupled to the server and/or client systems. The database systems and/or storage structures may be remote from or local to the computer or other processing systems, and may store any desired data (e.g., data relating to substance administration).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create mechanisms for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method of managing administration of substances comprising:
receiving, via a processor, information including administration of one or more substances and user preferences for the administration, wherein the one or more substances have been administered to a user;

extracting, via the processor, features of the received information and identifying interactions between the one or more substances and a new substance for administration based on the extracted features, wherein the new substance includes one or more of: a food item and a beverage, and wherein the features are extracted by accessing a database to identify the features of the one or more substances and to determine interactions between the identified features;

performing machine learning to train a genetic learning model using a fitness function that is assigned to a set of learned categories of combinations of administered substances; and generating, via the processor, a schedule for administration of the one or more substances and the new substance based on the interactions, wherein the schedule is generated using the trained genetic learning model by evaluating the new substance against the one or more substances, wherein the schedule is based on half-lives of the one or more substances and the new substance, and wherein the schedule includes a recommendation of an additional substance that is complementary to the new substance, wherein generating the schedule comprises modifying a previous schedule that is based on the one or more substances that have been administered to the user, wherein the new substance is not included in the previous schedule and is included in the schedule in response to the user logging administration of the new substance, and wherein the one or more substances includes insulin that is administered to treat diabetes of the user.

2. The computer-implemented method of claim 1, wherein the generated schedule indicates one or more from a group of: time, dosage, and a complementary sub stance for administration.

3. The computer-implemented method of claim 1, wherein user preferences include one or more from a group of: time for administering medication and a complementary sub stance.

4. The computer-implemented method of claim 1, wherein receiving the information comprises one or more from a group of:
   scanning a label of medication;
   retrieving RFID signals indicating a medication;
   retrieving activity on social media sites; and
   retrieving substance information from an electronic medical record.

5. The computer-implemented method of claim 1, wherein the substances include one or more from a group of prescription medication, over-the-counter medication, home remedies, herbal substances, beverages, nutraceuticals, and food.

6. The computer-implemented method of claim 1, further comprising:
   recording, via the processor, a time of administration of a substance; and
   providing, via the processor, a notification to administer the substance at the recorded time.

7. The computer-implemented method of claim 1, wherein the schedule is further generated using multi-dimensional allocation and optimization techniques.

8. The computer-implemented method of claim 1, further comprising:
   dynamically adjusting, via the processor, the schedule based on consumption patterns of the one or more substances.

9. A computer system for managing administration of substances, the computer system comprising:
   one or more computer processors;
   one or more computer readable storage media;
   program instructions stored on the one or more computer readable storage media for execution by at least one of the one or more computer processors, the program instructions comprising instructions to:
   receive information including administration of one or more substances and user preferences for the administration, wherein the one or more substances have been administered to a user;
   extract features of the received information and identifying interactions between the one or more substances and a new substance for administration based on the extracted features, wherein the new substance includes one or more of: a food item and a beverage, and wherein the features are extracted by accessing a database to identify the features of the one or more substances and to determine interactions between the identified features;
   perform machine learning to train a genetic learning model using a fitness function that is assigned to a set of learned categories of combinations of administered substances; and
   generate a schedule for administration of the one or more substances and the new substance based on the interactions, wherein the schedule is generated using the trained genetic learning model by evaluating the new substance against the one or more substances, wherein the schedule is based on half-lives of the one or more substances and the new substance, and wherein the schedule includes a recommendation of an additional substance that is complementary to the new substance, wherein generating the schedule comprises modifying a previous schedule that is based on the one or more substances that have been administered to the user, wherein the new substance is not included in the previous schedule and is included in the schedule in response to the user logging administration of the new substance, and wherein the one or more substances includes insulin that is administered to treat diabetes of the user.

10. The computer system of claim 9, wherein the generated schedule indicates one or more from a group of: time, dosage, and a complementary substance for administration.

11. The computer system of claim 9, wherein user preferences include one or more from a group of: time for administering medication and a complementary substance.

12. The computer system of claim 9, wherein receiving the information comprises one or more from a group of:
   scanning a label of medication;
   retrieving RFID signals indicating a medication;
   retrieving activity on social media sites; and
   retrieving substance information from an electronic medical record.

13. The computer system of claim 9, further comprising instructions to:
   record a time of administration of a substance; and
   provide a notification to administer the substance at the recorded time.

14. The computer system of claim 9, wherein the schedule is further generated using
multi-dimensional allocation and optimization techniques.

15. The computer system of claim 9, further comprising instructions to:
dynamically adjust the schedule based on consumption patterns of the one or more substances.

16. A computer program product for managing administration of substances, the computer program product comprising one or more non-transitory computer readable storage media collectively having program instructions embodied therewith, the program instructions executable by a computer to cause the computer to:
receive information including administration of one or more substances and user preferences for the administration, wherein the one or more substances have been administered to a user;
extract features of the received information and identifying interactions between the one or more substances and a new substance for administration based on the extracted features, wherein the new substance includes one or more of a food item and a beverage, and wherein the features are extracted by accessing a database to identify the features of the one or more substances and to determine interactions between the identified features;
perform machine learning to train a genetic learning model using a fitness function that is assigned to a set of learned categories of combinations of administered substances; and
generate a schedule for administration of the one or more substances and the new substance based on the interactions, wherein the schedule is generated using the trained genetic learning model by evaluating the new substance against the one or more substances, wherein the schedule is based on half-lives of the one or more substances and the new substance, and wherein the schedule includes a recommendation of an additional substance that is complementary to the new substance, wherein generating the schedule comprises modifying a previous schedule that is based on the one or more substances that have been administered to the user, wherein the new substance is not included in the previous schedule and is included in the schedule in response to the user logging administration of the new substance, and wherein the one or more substances includes insulin that is administered to treat diabetes of the user.

17. The computer program product of claim 16, wherein the generated schedule indicates one or more from a group of: time, dosage, and a complementary substance for administration.

18. The computer program product of claim 16, wherein user preferences include one or more from a group of: time for administering medication and a complementary substance.

19. The computer program product of claim 16, wherein receiving the information comprises one or more from a group of:
scanning a label of medication;
retrieving RFID signals indicating a medication;
retrieving activity on social media sites; and
retrieving substance information from an electronic medical record.

20. The computer program product of claim 16, wherein the schedule is further generated using
multi-dimensional allocation and optimization techniques.

* * * * *